United States Patent
Hagihara et al.

(10) Patent No.: US 11,129,595 B2
(45) Date of Patent: Sep. 28, 2021

(54) ULTRASONIC DIAGNOSTIC APPARATUS, INTERPOLATION PROCESSING UNIT, AND INTERPOLATION PROCESSING METHOD

(71) Applicant: TOSHIBA MEDICAL SYSTEMS CORPORATION, Otawara (JP)

(72) Inventors: Teruki Hagihara, Nasushiobara (JP); Wataru Kameishi, Nasushiobara (JP); Hiroyuki Shibanuma, Yaita (JP); Masaaki Ishitsuka, Nasushiobara (JP); Shuta Fujiwara, Nasushiobara (JP); Satoshi Kamiyama, Otawara (JP); Tomohiro Fujita, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 1006 days.

(21) Appl. No.: 14/920,147

(22) Filed: Oct. 22, 2015

(65) Prior Publication Data

US 2016/0120512 A1     May 5, 2016

(30) Foreign Application Priority Data

Oct. 31, 2014    (JP) .............................. JP2014-222534

(51) Int. Cl.
*A61B 8/08*          (2006.01)
*A61B 8/00*          (2006.01)
(Continued)

(52) U.S. Cl.
CPC .......... *A61B 8/5207* (2013.01); *A61B 8/4477* (2013.01); *G01S 7/52028* (2013.01);
(Continued)

(58) Field of Classification Search
CPC ............... A61B 8/5207; G01S 15/8925; G01S 7/52047; G01S 7/52038; G01S 15/8913;
(Continued)

(56) References Cited

U.S. PATENT DOCUMENTS

| 5,345,426 A * | 9/1994 | Lipschutz ........... G01S 7/52025 367/103 |
| 5,490,511 A | 2/1996 | Amemiya et al. |

(Continued)

FOREIGN PATENT DOCUMENTS

| JP | 1993-184568 A | * | 7/1993 | ............... A61B 8/00 |
| JP | 05184568 A | * | 7/1993 | ............... A61B 8/00 |

(Continued)

OTHER PUBLICATIONS

Viola et al. 2008 IEEE Trans. Ultrason. Ferroelectr. Freq. Control 55:2084-2091 (Year: 2008).*

(Continued)

*Primary Examiner* — Michael J Tsai
*Assistant Examiner* — Patrick M Mehl
(74) *Attorney, Agent, or Firm* — Oblon, McClelland, Maier & Neustadt, L.L.P.

(57) ABSTRACT

According to one embodiment, an ultrasonic diagnostic apparatus includes at least a memory circuitry, a processing circuitry, a data interpolation circuitry, and an image generating circuitry. The memory circuitry stores a plurality of pieces of reception data in an order of reception, the plurality of pieces of reception data being received continuously in a time series by a plurality of transducers, and specifies reading positions in an order different from the order of reception. The processing circuitry calculates a delay time, and calculates, based on the delay time, reading positions for acquiring reception data being used for calculating interpolation data from the memory circuitry. The data interpolation circuitry calculates interpolating data based on the plurality of pieces of reception data acquired from the calculated reading positions of the memory circuitry. The image generating circuitry generates an ultrasonic image based on a reception beam formed by using the interpolation data.

14 Claims, 10 Drawing Sheets

(51) Int. Cl.
*G01S 15/89* (2006.01)
*G01S 7/52* (2006.01)
*G10K 11/34* (2006.01)

(52) U.S. Cl.
CPC ........ *G01S 15/8915* (2013.01); *G10K 11/346* (2013.01); *A61B 8/461* (2013.01); *A61B 8/5215* (2013.01)

(58) Field of Classification Search
CPC .. G01S 15/8915; G01S 7/4915; G01S 7/2806; G01S 7/4865; G01S 7/287; G10K 11/346; G02B 7/40; A61N 7/00
See application file for complete search history.

(56) References Cited

U.S. PATENT DOCUMENTS

| | | | | |
|---|---|---|---|---|
| 5,684,484 A | * | 11/1997 | Suzuki | ................ G01S 7/52028 341/155 |
| 2012/0232834 A1 | * | 9/2012 | Roche | .................... A61B 34/20 702/150 |
| 2014/0121519 A1 | | 5/2014 | Miyajima et al. | |

FOREIGN PATENT DOCUMENTS

| JP | 2004-166745 A | * | 6/2004 | ............... A61B 8/00 |
|---|---|---|---|---|
| JP | 2010-115418 | | 5/2010 | |
| JP | 2012-205825 | | 10/2012 | |
| JP | 2013-31654 | | 2/2013 | |

OTHER PUBLICATIONS

Office Action dated May 8, 2018 in Japanese Patent Application No. 2014-222534.

* cited by examiner

ULTRASONIC DIAGNOSTIC APPARATUS, INTERPOLATION PROCESSING UNIT, AND INTERPOLATION PROCESSING METHOD

CROSS-REFERENCE TO RELATED APPLICATIONS

This application claims the benefit of priority of Japanese Patent Application No. 2014-222534, filed Oct. 31, 2014, the entire contents of which are incorporated herein by reference.

FIELD

Embodiments described herein relate generally to an ultrasonic diagnostic apparatus, an interpolation processing unit, and an interpolation processing method.

BACKGROUND

In medical fields, ultrasonic diagnostic apparatuses for imaging the interior of an object are being used in which an ultrasonic wave generated by using a plurality of transducers (piezoelectric transducers) of an ultrasonic probe is utilized. The ultrasonic wave generated by the transducer is reflected in an object, and acquired as a reception signal by each transducer. Particularly, in a digital beam forming, the reception signal acquired by each transducer is sampled at a predetermined sampling interval and converted into reception data which is digital data. Then, the reception data acquired by each transducer is synthesized to form a reception beam. The reception data received at each transducer is received at a different delay time depending on orienting direction of the reception beam and the distance between the transducer and the focal position. Accordingly, in the digital beam forming, delay times of the reception data received at respective transducers are made uniform, and then the pieces of reception data are added together to form a reception beam.

In a conventional ultrasonic diagnostic apparatus, the reception data is stored in time series in a receiving order in an FIFO (First In First Out) memory provided in each transducer. Then, by controlling the reading position from the FIFO memory, the delay times which differ from each other for each transducer are made uniform by coarse adjustment in the unit of a sampling interval. Further, by interpolating data within the sampling interval by an FIR (Finite Impulse Response) filter, the delay times of each transducer are made uniform by fine adjustment with an accuracy of the sampling interval or less. Thereafter, the pieces of reception data are added to form a reception beam.

As described above, in a conventional ultrasonic diagnostic apparatus, interpolation data has been generated by inputting a plurality of pieces of sampling data (for example, four successive pieces of sampling data) read out from the FIFO memory into an FIR filter having multiple taps (for example, 4 taps) in time series. This interpolation data is generated for each transducer, that is, for each reception channel, and the pieces of interpolation data generated at each reception channel are added to form a reception beam. However, there may be a case in which the reception data which is needed for performing fine adjustment of delay times of each transducer with an accuracy of a sampling interval or less is not in the order of time series. For example, when four pieces of sampling data of "5", "6", "7", and "8" are inputted into the FIR filter, it is supposed that data between "6" and "7" (for example, 6.3, etc.) can be interpolated. When data to be interpolated next is between "8" and "9" (for example, 8.5 etc.), required data will be "7", "8", "9", and "10". Since pieces of data are stored in the order of time series in an FIFO memory, the pieces of sampling data which can be acquired following "5", "6", "7", and "8" are "6", "7", "8", and "9". In this way, in a conventional FIR filter, when pieces of data to be interpolated are spaced apart by one or more sampling points, there is a case where necessary data cannot be read, and interpolation data cannot be calculated.

A conventional ultrasonic diagnostic apparatus is configured such that by setting a sampling interval large, it is made possible to calculate interpolation data within a range of sampling data read into the FIR filter. However, increasing the sampling interval tends to cause deterioration of image quality of the ultrasonic image to be finally generated.

Thus, there is a need for an ultrasonic diagnostic apparatus, an interpolation processing unit, and an interpolation processing method, which can concurrently and collectively acquire reception data which is necessary for interpolation, without increasing the sampling interval.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an ultrasonic diagnostic apparatus, an interpolation processing unit, and an interpolation processing method according to embodiments of the present invention with reference to the drawings.

In general, according to one embodiment, an ultrasonic diagnostic apparatus includes a plurality of transducers, a memory circuitry, a processing circuitry, a data interpolation circuitry, and an image generating circuitry. The plurality of transducers transmits an ultrasonic wave and receives a reflected wave from an interior of an object. The memory circuitry stores a plurality of pieces of reception data in an order of reception, the plurality of pieces of reception data being received continuously in a time series, and specifies reading positions in an order different from the order of reception. The processing circuitry calculates a delay time to be set for every reception data from each of the plurality of transducers, and calculates, based on the delay time, reading positions for acquiring a plurality of pieces of reception data to be used for calculating interpolation data from the memory circuitry. The data interpolation circuitry calculates interpolating data based on the plurality of pieces of reception data acquired from the calculated reading positions of the memory circuitry. The image generating circuitry generates an ultrasonic image based on a reception beam formed by using the interpolation data.

(1) Configuration

Figure 1:
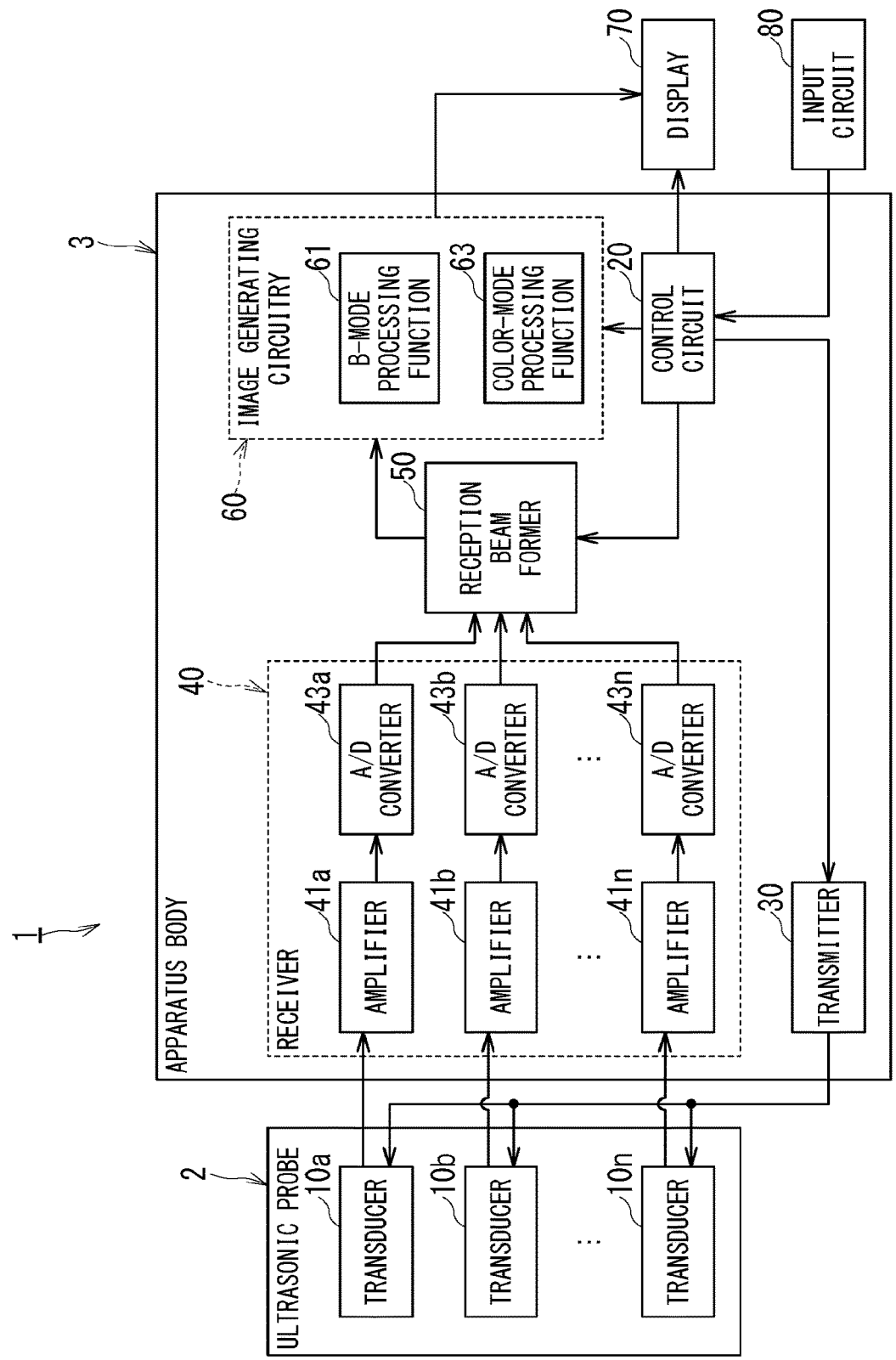
FIG. 1 is a schematic block diagram to show an example of an ultrasonic diagnostic apparatus relating to an embodiment.

FIG. 1 is a schematic block diagram to show an example of an ultrasonic diagnostic apparatus 1 relating to an embodiment. As shown in FIG. 1, the ultrasonic diagnostic apparatus 1 comprises an ultrasonic probe 2, an apparatus body 3, a display 70, and an input circuit 80.

The ultrasonic probe 2 is connected with the apparatus body 3 via a cable etc. and transmits an ultrasonic wave into an object by bringing its distal end thereof into contact with the body surface of the object. The ultrasonic probe 2 includes at its distal end a plurality of transducers 10 (10a, 10b . . . 10n) which transmit and receive an ultrasonic signal.

A plurality of (N) transducers 10 are arranged one-dimensionally in a distal end portion of the ultrasonic probe 2. The transducer 10, which is an electroacoustic transducer, has a function of converting an electric pulse into an ultrasonic pulse (transmitted ultrasonic wave) at the time of transmission, and converting an ultrasonic reflected wave (received ultrasonic wave) into an electric signal (reception signal) at the time of reception. Note that the arrangement of the transducers is not limited to be one-dimensional, and may also be arranged to be two-dimensional.

The apparatus body 3 comprises a control circuit 20, a transmitter 30, a receiver 40, a reception beam former 50, and an image generating circuitry 60.

The control circuit 20 includes a processor such as a CPU (Central Processing Unit), and a storage apparatus and comprehensively controls each portion of the ultrasonic diagnostic apparatus 1.

The transmitter 30 generates a transmission signal for radiating transmitted ultrasonic wave according to the control of the control circuit 20. As a result of each transducer 10 being driven based on the generated transmission signal, a transmitted ultrasonic wave is radiated into a living body.

The receiver 40 inputs reception signals from a living body received from the respective transducers 10 (10a, 10b . . . 10n) into amplifiers 41 (41a, 41b . . . 41n), and coverts the amplified reception signals into digital data with A/D converters 43 (43a, 43b . . . 43n).

Note that in the example of FIG. 1, although the transmitter 30 and the receiver 40, which give and receive signals to and from the transducers 10, and the reception beam former 50 are constructed in the apparatus body 3, they may be constructed in the ultrasonic probe 2.

The reception beam former 50 calculates interpolation data from the reception data sampled at the receiver 40 according to delay times, executing phasing addition processing and thereby forms a reception beam. Hereafter, data for which delay times are made uniform based on the reception data is referred to as interpolation data. The reception beam former 50 forms a reception beam for each orienting direction of the reception beam by adding all the interpolation data for each focal position.

The image generating circuitry 60 includes a processor and a memory circuitry. The processor of the image generating circuitry 60 realizes a B-mode processing function 61 and a color-mode processing function 63 by executing programs stored in the storage circuit, and generates an ultrasonic image such as B-mode data, color Doppler data, and Doppler spectrum based on obtained reception beams. The image generating circuitry 60 generates a B-mode image and a color Doppler image as an ultrasonic image by saving B-mode data and color-Doppler data in correspondence with the scanning direction, and generates a Doppler spectrum image and an M-mode image as an ultrasonic image by saving the Doppler spectrum and B-mode data obtained in the predetermined scanning direction in time series.

The display 70 displays the generated ultrasonic image, etc. according to the control of the control circuit 20.

The input circuit 80 includes various switches, buttons, a track ball, a touch panel, a mouse, and a key board, etc. for taking in various instructions from the operator, conditions, setting instruction of region of interest (ROI), and various image quality conditions setting instruction etc. into the ultrasonic diagnostic apparatus 1.

Figure 2:
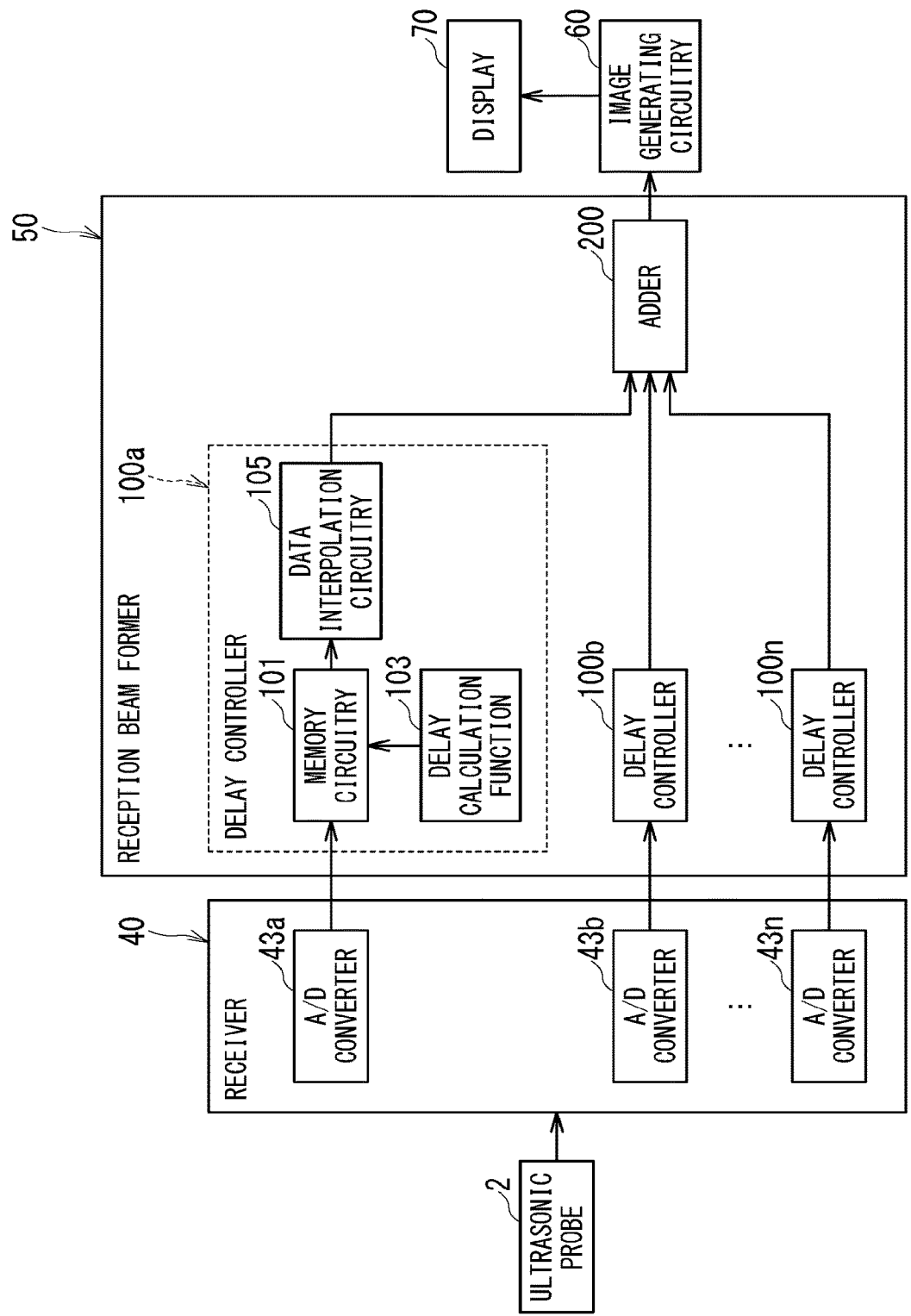
FIG. 2 is a functional block diagram to show an example of the functional configuration of the reception beam former of the ultrasonic diagnostic apparatus relating to an embodiment.

FIG. 2 is a functional block diagram to show an example of the functional configuration of the reception beam former 50 of the ultrasonic diagnostic apparatus 1 relating to an embodiment. The reception beam former 50 comprises a delay controller 100 (100a, 100b . . . 100n) and an adder 200. A number of delay controllers 100 corresponding to the number of transducers 10 are constructed in the reception beam former 50.

The delay controller 100 has a memory circuitry 101, as well as a processing circuitry which includes at least a processor and a storage circuitry. The processing circuitry of the delay controller 100 implements a delay calculation function 103 by executing a program stored in the storage circuitry. Moreover, the delay controller 100 further has a data interpolation circuitry 105. Note that the delay calculation function 103 of the delay controller 100 may be implemented by hardware logic without using a processor. Moreover, the data interpolation circuitry 105 of the delay controller 100, and the adder 200 may be replaced by a function which is implemented by a processor executing a program.

The memory circuitry 101 is configured to store a plurality of pieces of reception data in an order of reception, the plurality of pieces of reception data being received continuously in a time series, and to be able to be specified reading positions which are in an order different from the order or reception. The reception signal received at the receiver 40 is amplified by the amplifier 41, and is thereafter converted into digital data by an A/D converter 43 to be accumulated in the memory circuitry 101 as reception data. The memory circuitry 101 divides and stores reception data for each data set so as to be able to concurrently and collectively read out the data which is needed in the data interpolation circuitry 105. The method of storing the reception data in the memory circuitry 101 will be described below.

The delay calculation function 103 which is implemented by the processing circuitry of the delay controller 100 is a function of calculating a delay time to be set for each reception data from each of a plurality of transducers (10a, 10b . . . 10n), and based on the delay time, calculating reading positions for acquiring a plurality of pieces of reception data, which are used for calculation of interpolation data, from the memory circuitry 101. For example, the delay calculation function 103 calculates a delay time according to the orienting direction of the reception beam and the distance between each focal position and each transducer 10, and based on the delay time, calculates reading positions for acquiring reception data, which are needed for calculating interpolation data from the memory circuitry 101. The delay time changes according to the orienting direction of the reception beam to be formed, as well as to the distance between the focal point and each transducer 10 for receiving signals. Each reception beam is formed by adding the reception data received at each transducer 10 with the delay time thereof being made uniform. Note that although, in FIG. 2, an example in which the delay calculation function 103 exists for each delay controller 100, the delay calculation function 103 may exist as a common configuration for all the delay controllers 100. The delay time will be described later.

The data interpolation circuitry 105 includes, for example, an interpolation filter which weights a plurality of pieces of reception data acquired from the memory circuitry 101 with respective coefficients, and thereafter adds them to calculate interpolation data. When making the data, which is to be added to form the reception data, be uniform according to delay times, it becomes necessary to interpolate the reception data which is digital data. The data interpolation circuitry 105 acquires some of the pieces of reception data (hereafter, referred to as sampling data) to calculate interpolation data. The calculation of the interpolation data will be described later.

The adder 200 adds interpolation data calculated at each focal position to form a reception beam at each focal position. Based on thus formed reception beam, an ultrasonic image is generated in the image generating circuitry 60.

(2) Operation

Hereafter, a method of storing reception data in a memory and a method of interpolating data will be described as a "first embodiment", and in addition to the first embodiment, a method of interpolating data, in which when the reception data acquired from the memory overlaps, only difference data (a subtractive difference thereof) is acquired from the memory is described as a "second embodiment".

First Embodiment

The first embodiment relates to a method of storing reception data in a memory, and a method of interpolating data.

Figure 3:
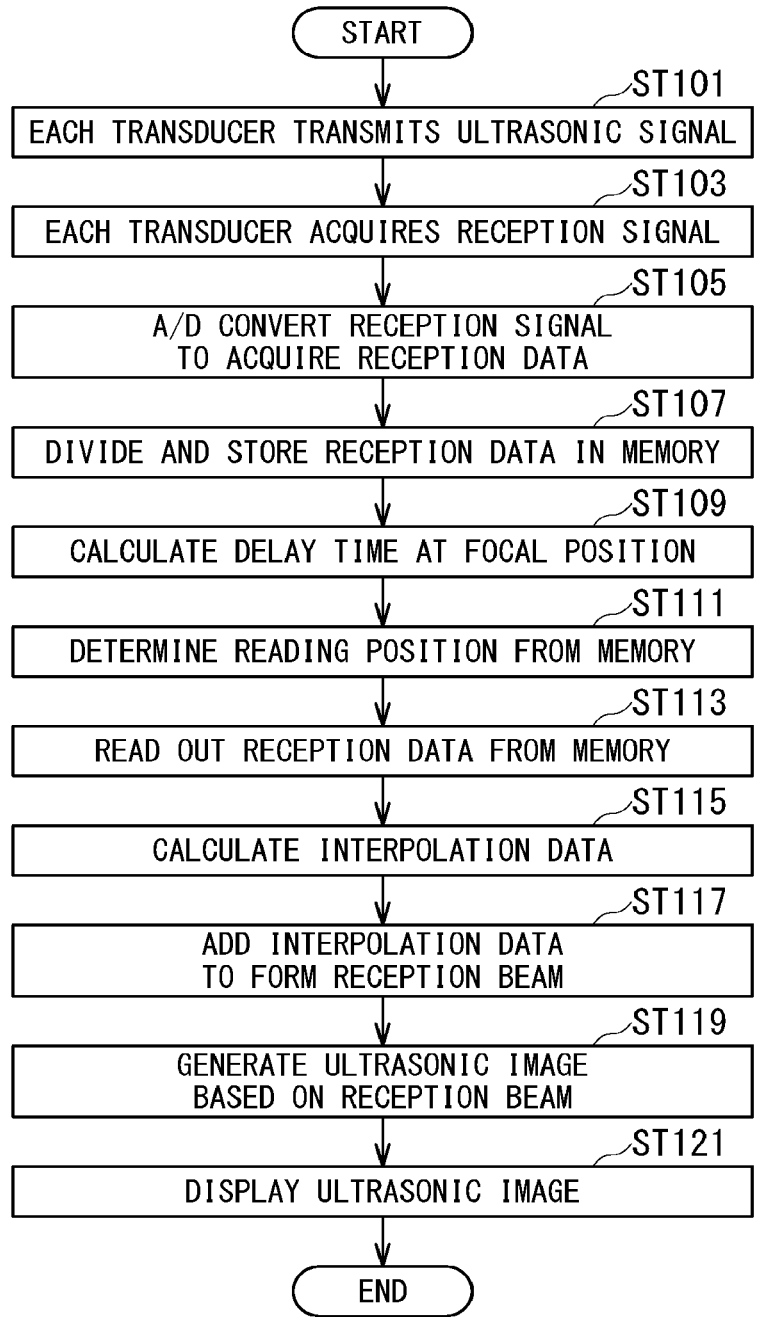
FIG. 3 is a flow chart to show an example of the operation of the ultrasonic diagnostic apparatus relating to the first embodiment.

FIG. 3 is a flow chart to show an example of the operation of the ultrasonic diagnostic apparatus 1 relating to the first embodiment.

In ST101, an ultrasonic signal is transmitted from each transducer 10.

In ST103, each transducer 10 acquires a reception signal.

In ST105, the signal acquired by each transducer 10 is amplified by the amplifier 41, and reception data which is digitally converted by the A/D converter 43 is acquired.

In ST107, the memory circuitry 101 divides and stores the reception data.

In ST109, the delay calculation function 103 calculates a delay time.

In ST111, the delay calculation function 103 determines reading positions of the reception data from the memory circuitry 101 according to the delay time.

Figure 4B:
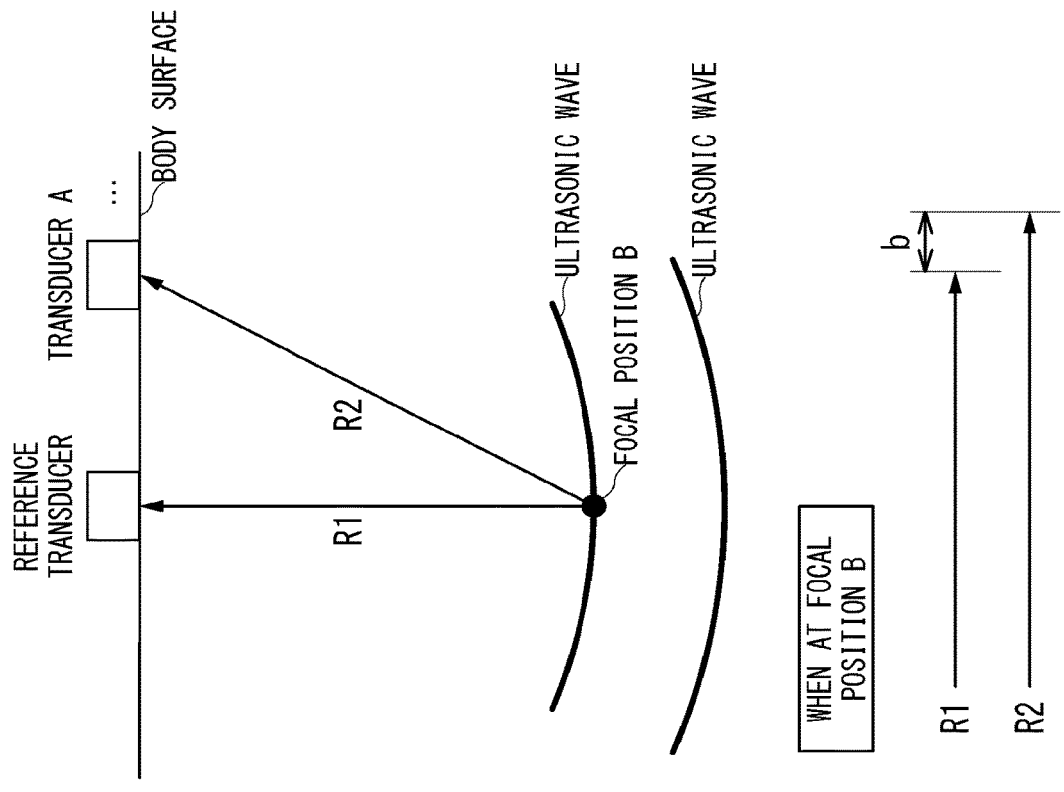
FIG. 4B shows a case of a focal position B, in which the focal positions A and B are different in the distance from the body surface of the object.
Figure 4A:
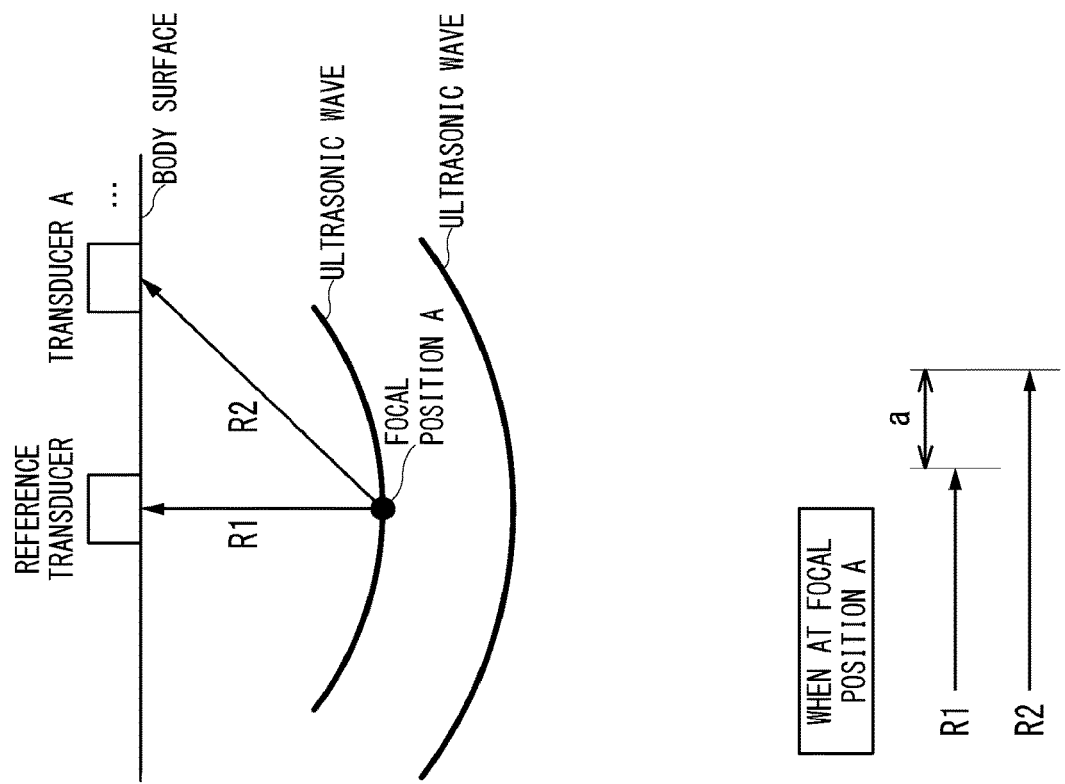
FIG. 4A shows a case of a focal position A.

FIGS. 4A and 4B are diagrams to illustrate the delay time of the ultrasonic diagnostic apparatus 1. FIG. 4A shows a case of a focal position A, and FIG. 4B shows a case of a focal position B, in which the focal positions A and B are different in the distance from the body surface of the object. FIGS. 4A and 4B show ultrasonic waves transmitted from the transducer 10. FIGS. 4A and 4B show, in the upper portions thereof, a reference transducer and a transducer A. The reference transducer is a transducer which serves as a reference when calculating delay time, and in FIGS. 4A and 4B, the transducer A is another transducer 10 with reference to the reference transducer. FIGS. 4A and 4B describe the delay times of the reference transducer and the transducer A.

FIG. 4A shows a distance (R1) from the focal position A to the reference transducer, and a distance (R2) from the focal position A to the transducer A. As shown by the lengths of arrows of R1 and R2 shown in the lower portion of FIG. 4A, the distance from the focal position A varies depending on the position of the transducer 10. For example, when an ultrasonic wave transmitted from the reference transducer is received by the reference transducer and the transducer A, the delay times of the reference transducer is (R1+R1)/Vs, and the delay time of the transducer A will become (R1+R2)/Vs (where, Vs indicates an ultrasound velocity in an object). That is, the reception timing of the transducer A is delayed by an amount corresponding to the difference in distance R2−R1 compared with the reference transducer. In this way, when the distance from the focal position to the transducer 10 is different, the timing to receive a reception signal at each transducer 10 will be different. The ultrasonic diagnostic apparatus 1 adjusts such difference in the reception timing which differs in each transducer 10 based on delay times.

FIG. 4B shows a distance (R1) from the focal position B to the reference transducer, and a distance (R2) from the focal position B to the transducer A. The focal position B is located at a deeper position than the focal position A shown in FIG. 4A. FIG. 4B, as well as FIG. 4A, shows that the delay time differs depending on the distance between the focal position and the transducer.

Arrows shown in the lower portion of FIGS. 4A and 4B indicate the difference in the distance from the focal position between the transducers to the transducer (that is, difference in reception timing). The arrow shown in the lower portion of FIG. 4A indicates a difference "a" of the distance R1 from the focal position A to the reference transducer, and the distance R2 from the focal position A to the transducer A. Similarly, the lower portion of FIG. 4B indicates a difference "b" of the distance R1 from the focal position B to the reference transducer and the distance R2 from the focal position B to the transducer A.

As shown in the lower portion of FIGS. 4A and 4B, when the focal position is deep (focal position B), the difference in the distance from the focal position to each transducer becomes smaller compared with when the focal position is shallow (focal position A). In this way, the difference in the delay time generated between transducers is not fixed and varies depending on the focal position.

In a digital beam forming, each transducer receives reception signals concurrently and in parallel from focal positions of a plurality of orienting directions, and of a plurality of depths to generate an ultrasonic image. Therefore, the delay calculation function 103 calculates delay times for each focal position which is present in multiple numbers in each orienting direction. For example, in the example of FIGS. 4A and 4B, the delay time (R1+R1)/Vs of the reference transducer and the delay time (R1+R2)/Vs of the transducer A are calculated, and based on these delay times, the reception data of each transducer 10 is made uniform to form a reception beam. However, since the reception data is digital data, and is acquired according to a sampling interval conforming to a sampling theorem, data corresponding to the sampling data of the reference transducer may become data between sampling data at another transducer 10. In such a case, it is necessary to determine data by interpolation based on the sampling data.

Figure 5:
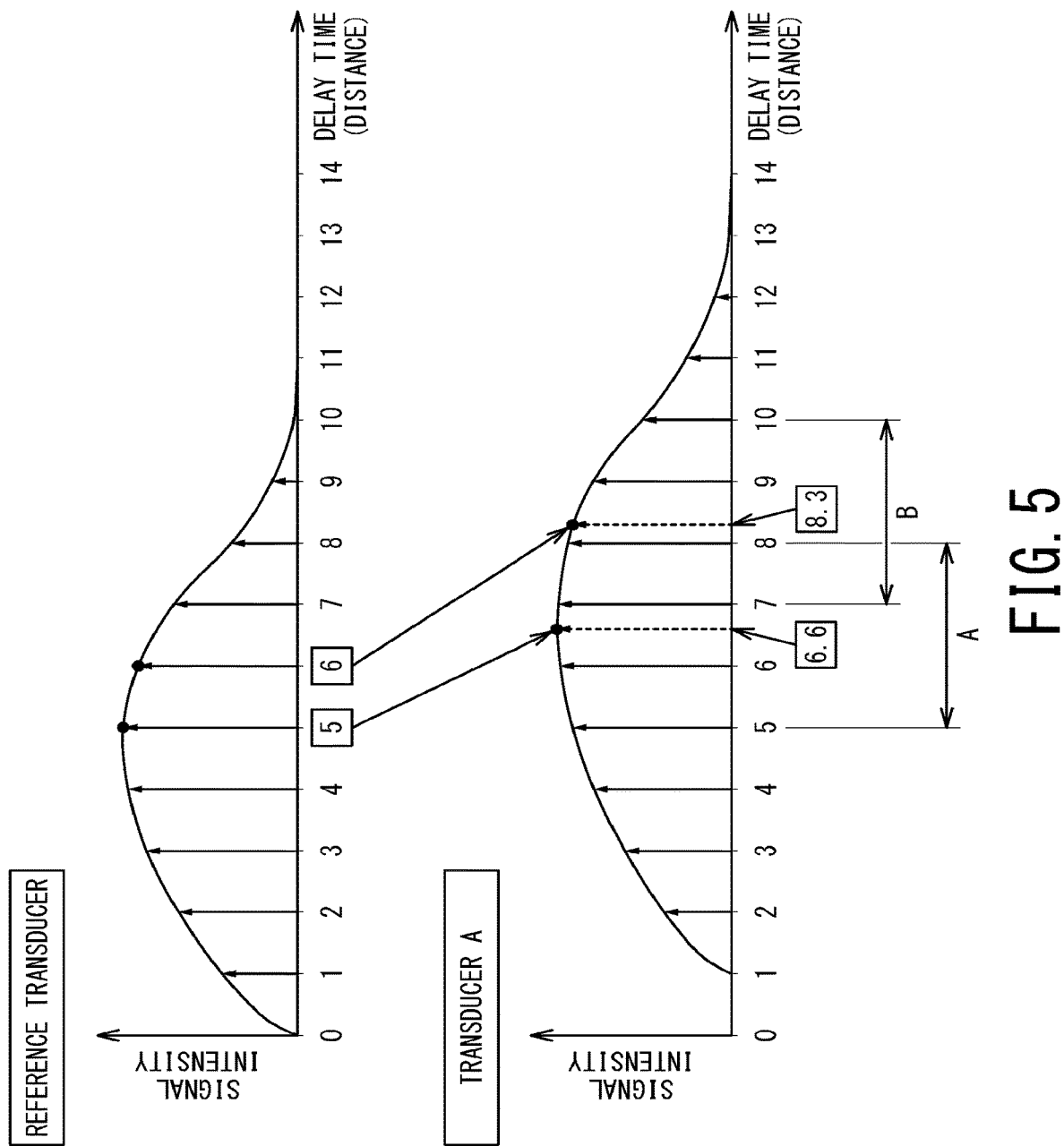
FIG. 5 illustrates the need of the data interpolation in the formation of reception beam.

FIG. 5 illustrates the need of the data interpolation in the formation of reception beam. FIG. 5 shows an example in which the reception signals received by the reference transducer and the transducer A illustrated in FIGS. 4A and 4B are sampled at a constant time interval. The ordinate of each graph shows the signal intensity of the reception signal, and the abscissa shows the delay time (distance). Here, the distance refers to the distance in the depth direction from the transducer 10 to the focal position. As shown in FIGS. 4A and 4B, the delay time varies depending on the distance between the focal position and the transducer 10. Note that a numerical value of the abscissa shows a sampling point, and a numerical value shown with quotation marks (" ") in the following description indicates a sampling number of the reception data corresponding to the distance (that is, the distance of the focal position in the depth direction of the object). Therefore, data of "5" means the sampling data (reception data) corresponding to "distance 5".

The upper half of FIG. 5 shows sampling data of the reference transducer shown in FIGS. 4A and 4B. For example, it is supposed that data "5" of FIG. 5 is a sampling point corresponding to the delay time (R1+R1)/Vs of the reference transducer at the focal position A shown in FIG. 4A, and "6" of FIG. 5 is the sampling point at the focal position B shown in FIG. 4B.

Similarly, the lower half of FIG. 5 shows the sampling data of the reference transducer A shown in FIGS. 4A and 4B. In the lower half of FIG. 5, the data of the transducer A corresponding to the sampling point "5" of the reference transducer is located at a position between the sampling points "6" and "7" (for example, 6.6). Similarly, the data of the transducer A corresponding to the sampling point "6" of the reference transducer is located at a position between the sampling points "8" and "9" (for example, 8.3).

A reception beam is formed by adding the reception data of each focal position of each transducer with the delay times thereof being made uniform. The data at a position of "6.6" and the data at a position of "8.3" of the transducer A are not included in the sampling data because they are located between sampling points. Therefore, these data need to be calculated by interpolation processing.

For example, when interpolation data is calculated by using four pieces of data, the interpolation processing is performed based on two pieces of data before and after centering on the interpolation data to be calculated. That is, in FIG. 5, to interpolate the data of a position of "6.6" of the transducer A, the pieces of reception data of the sampling points of "5", "6", "7", and "8" are used (in the range of arrow A). Similarly, to interpolate the data of a position of "8.3" of the transducer A, the pieces of reception data of the sampling points of "7", "8", "9", and "10" are used (in the range of arrow B).

Thus, the delay calculation function 103 calculates the delay time of each transducer 10 (ST109), and determines the position of necessary interpolation data according to the calculated delay time. Further, by determining the sampling data before and after that position, the delay calculation function 103 determines reading positions from the memory circuitry 101 (ST111).

Referring back to FIG. 3, the calculation method of interpolation data and the formation of reception beam will be described further.

In ST113, the data interpolation circuitry 105 reads out reception data from the memory circuitry 101.

In ST115, the data interpolation circuitry 105 calculates interpolation data.

In ST117, the pieces of interpolation data calculated by the adder 200 are added to form a reception beam. The reception beam is formed at each focal position. Once a reception beam of a certain focal position is formed, a reception beam at a next focal position is formed successively. Note that there may be a case where calculation of interpolation data is not needed, and the reception data itself of the transducer 10 is available depending on the relationship between the transducer 10 and the focal position. In such a case, the reception beam may be formed by using both the reception data itself and the interpolation data.

In ST119, an ultrasonic image is generated based on the generated reception beam in the image generating circuitry 60. The reception beam is formed based on a plurality of directions, and a plurality of depths (focal positions), and an ultrasonic image is generated from those reception beams.

In ST121, an ultrasonic image is displayed on the display 70.

Hereafter, a method of calculating interpolation data and forming a reception beam will be described. While a reception beam is formed for each focal position, when for example, a reception beam is formed at a focal position B following the focal position A shown in FIGS. 4A and 4B, first, sampling data of "5" of the reference transducer and data of the position "6.6" of the transducer A are added to form a reception beam at a focal position A. Next, data of the sampling point "6" of the reference transducer and the data of the position "8.3" of the transducer A are added to form a reception data at a focal position B. Therefore, when calculating interpolation data, after using the sampling data of "5", "6", "7", and "8" to calculate interpolation data of "6.6", data of "7", "8", "9", and "10" are needed to calculate interpolation data of "8.3" which is the next interpolation data.

Figure 6A:
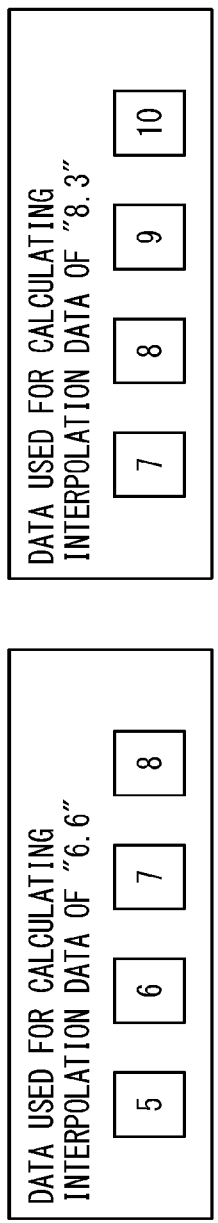
FIG. 6A shows sampling data which becomes necessary when calculating interpolation data ("6.6") in the focal position A of the transducer A and interpolating data ("8.3") at a focal position B as illustrated.
Figure 6B:
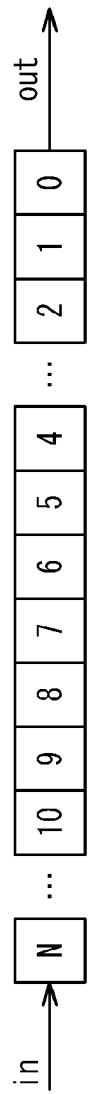
FIG. 6B is a diagram to illustrate a method of storing reception data for sampling points in an FIFO memory in a conventional ultrasonic diagnostic apparatus.
Figure 6C:
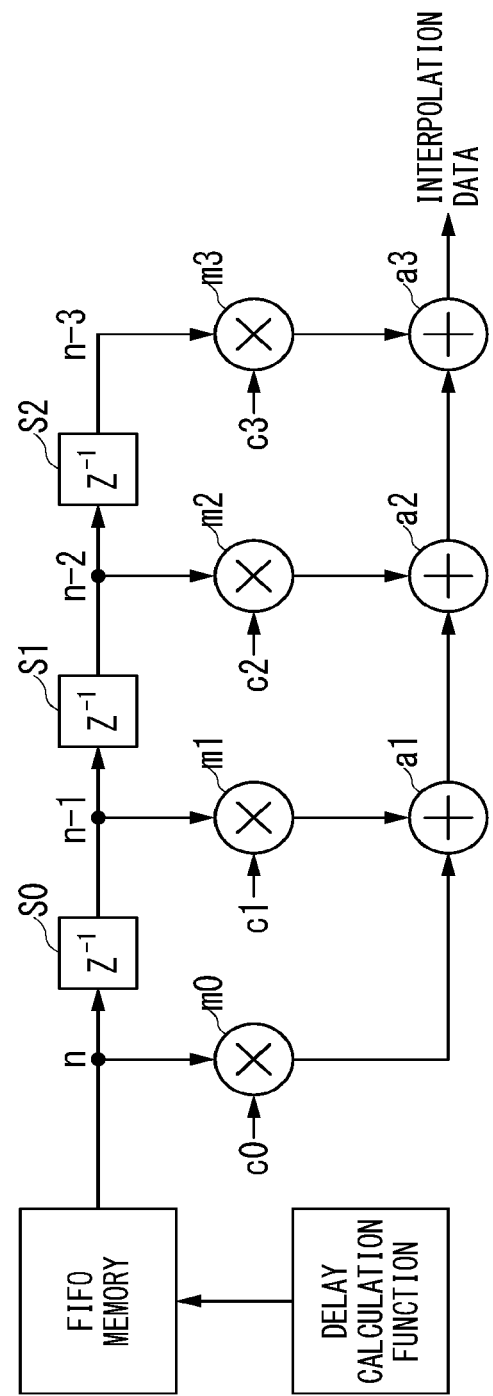
FIG. 6C shows an example of a digital circuit of an FIR filter.

FIGS. 6A, 6B and 6C are diagrams to illustrate a data interpolation method in a conventional ultrasonic diagnostic apparatus.

As shown in the left-side diagram in FIG. 6A, the interpolation data of a position of "6.6" of the transducer A is data between "6" and "7", and is calculated based on the reception data of sampling points of "5", "6", "7", and "8". Similarly, as shown in the right-side diagram in FIG. 6A, the interpolation data of the position of "8.3" of the transducer A is data between "8" and "9", and is calculated from the reception data of the sampling points of "7", "8", "9", and "10".

As shown in FIG. 6B, in a conventional ultrasonic diagnostic apparatus, reception data for each sampling point are stored in an FIFO memory. The FIFO memory is a memory in which data is stored from the right end in the order of input, and can be taken out in the order of input. For example, when reception data of "4" is taken out, the next data to be taken out will be reception data of "5". Therefore, after having calculated the interpolation data of a position of "6.6" of the transducer A from "5", "6", "7", and "8", the data which can be taken out next from the FIFO memory are "6", "7", "8", and "9". Therefore, it is not possible to concurrently and collectively acquire the reception data of "7", "8", "9", and "10" which are needed for calculating the interpolation data of "8.3" of the transducer A to be calculated next from the memory. In this way, upon forming a reception beam successively for each focal position, there may be a case, in a conventional ultrasonic diagnostic apparatus, in which the reception data needed for interpolation cannot be acquired.

FIG. 6C shows an example of a digital circuit of an FIR filter. FIG. 6C shows an example of the FIR filter having a tap number of 4. S0 to S2 each indicate a unit delay circuit, m0 to m3 each indicate a multiplication circuit to multiply the inputted reception data by a coefficient, and c0 to c3 each indicate a coefficient of the multiplication circuit. The reception data read from the FIFO memory is inputted to the multiplication circuits (m0, m1, m2, and m3) in the order of sampling by the unit delay circuit. A coefficient is set respectively for each multiplication circuit, and pieces of inputted reception data are weighted by the set coefficient. The reception data which has been weighted by the multiplication circuit is inputted to the adding circuits (a1, a2, and a3) to be added and outputted as interpolation data. For example, when calculating interpolation data of "6.6" (when n is "8") from the reception data of the sampling points "5", "6", "7", and "8", reception data of "5" (n−3) is inputted to m3 at the right end; the reception data of "6" (n−2) into m2; the reception data of "7" (n−1) into m1; and the reception data of "8" (n) into m0, respectively. The pieces of inputted reception data are weighted by the coefficients c0 to c3 set in the multiplication circuits m0 to m3, respectively and are added in the adding circuits a1 to a3 so that interpolation data of "6.6" is outputted.

As described above, after the interpolation data of "6.6" of the transducer A at a focal position A is calculated, it is necessary to calculate the interpolation data of "8.3" of the transducer A at a focal position B. Therefore, after the calculation using "5", "6", "7", and "8", the pieces of data needed next in the FIR filter are "7", "8", "9", and "10".

However, after the sampling points of "5", "6", "7", and "8" are read, the data which is next taken out from the FIFO memory will be the data of the sampling point "9". Therefore, the pieces of data of "6", "7", "8", and "9" are inputted into the FIR filter. For this reason, in a conventional ultrasonic diagnostic apparatus, after calculating "6.6", it is not possible to concurrently and collectively read the reception data needed for interpolating data, which is located at a position apart from the previous interpolation data by a distance of one or more sampling points, such as "8.3". In order to avoid such a case, a conventional ultrasonic diagnostic apparatus is configured such that sampling intervals are increased at sacrifice of image quality, making it possible to calculate the interpolation data by using the sampling data inputted into the FIFO memory according to time series.

On the other hand, the ultrasonic diagnostic apparatus 1 relating to the present embodiment solves the above described problem by a data interpolation method, in which reception data is stored in a memory in a different manner from in the FIFO memory, thereby allowing to concurrently and collectively take out data and input the reception data into an interpolation filter.

Figure 7A:
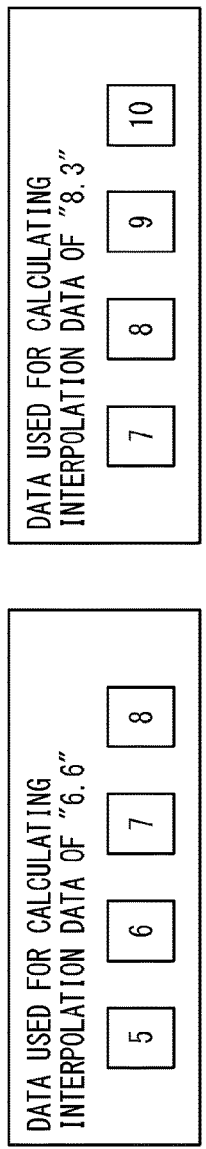
FIG. 7A shows sampling data which becomes necessary when calculating interpolation data ("6.6") in the focal position A of the transducer A and interpolating data ("8.3") at a focal position B as illustrated in FIG. 6A.
Figure 7B:
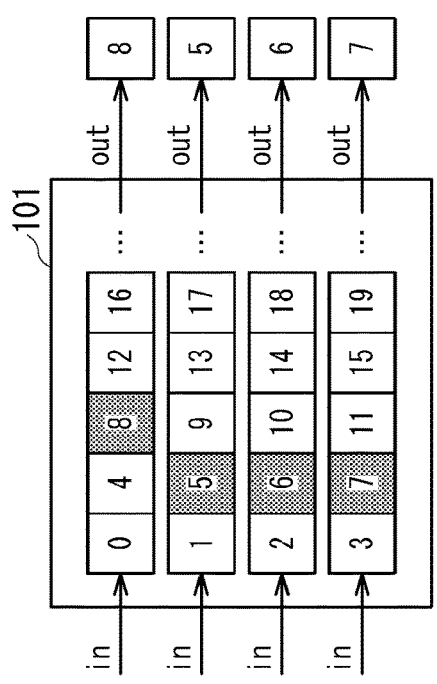
FIG. 7B is a diagram to illustrate a method of taking out sampling points of "5", "6", "7", and "8" from the memory circuitry according to a present embodiment.
Figure 7C:
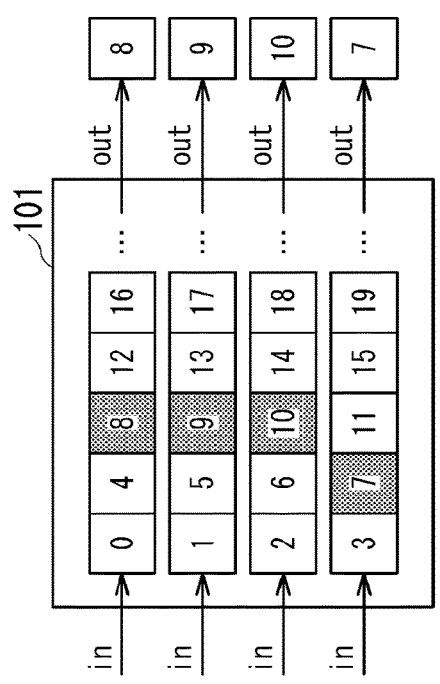
FIG. 7C is a diagram to illustrate a method of taking out sampling points of "7", "8", "9", and "10" from the memory circuitry according to the present embodiment.

FIGS. 7A, 7B and 7C are diagrams to illustrate data input and output in a memory of an ultrasonic diagnostic apparatus 1 relating to an embodiment. FIG. 7A, as well as FIG. 6A, shows sampling data which becomes necessary when calculating interpolation data ("6.6") in the focal position A of the transducer A and interpolating data ("8.3") at a focal position B as illustrated in FIGS. 6A, 6B and 6C. For example, when using an interpolation filter, which calculates interpolation data based on four pieces of reception data, as shown in the left-side diagram of FIG. 7A, the interpolation data "6.6", which is located between "6" and "7", is calculated based on the sampling data of "5", "6", "7", and "8". Similarly, as shown in the right-side diagram of FIG. 7A, the interpolation data of "8.3" which is located between "8" and "9", is calculated from the sampling data of "7", "8", "9", and "10".

FIG. 7B is a diagram to illustrate a method of taking out sampling points of "5", "6", "7", and "8" from the memory circuitry 101. The ultrasonic diagnostic apparatus 1 relating to the present embodiment divides reception data according to the number of pieces of data to be used in the data interpolation circuitry 105, and stores them in the memory circuitry 101. In the present embodiment, description will be made on an example in which when interpolation data is calculated based on four pieces of reception data, the reception data is divided into four data sets to be stored in the memory circuitry 101 such that the interval of data becomes four. To be specific, as shown in the first level of the memory circuitry 101 of FIG. 7B, sampling points "0", "4", "8", "12", "16", . . . are stored in a memory region as one data set, and similarly sampling points "1", "5", "9", "13", and "17" . . . are stored in a memory region as one data set. Storing in this way and reading necessary data one from each data set allows concurrent and collective acquisition thereof.

FIG. 7C is a diagram to illustrate a method of taking out sampling points of "7", "8", "9", and "10" from the memory circuitry 101. The reception data necessary for interpolation is stored in one for each data set. As a result of that, a plurality of pieces of reception data, which are arranged in time series, can be acquired concurrently and collectively without need of reading them one by one in the order of time series. That is, according to the configuration of the memory circuitry 101 of the embodiment, unlike a conventional ultrasonic diagnostic apparatus, there is no restriction that after reading out "5", "6", "7", and "8", the reception data needs to be read out by shifting them each time by one sampling point so as to be "7", "8", "9", and "10". Therefore, after reading out "5", "6", "7", and "8", it is possible to read out "7", "8", "9", and "10" concurrently and collectively by skipping one sampling point, and also possible to read out "8", "9", "10", and "11" by skipping 2 sampling points.

Figure 8:
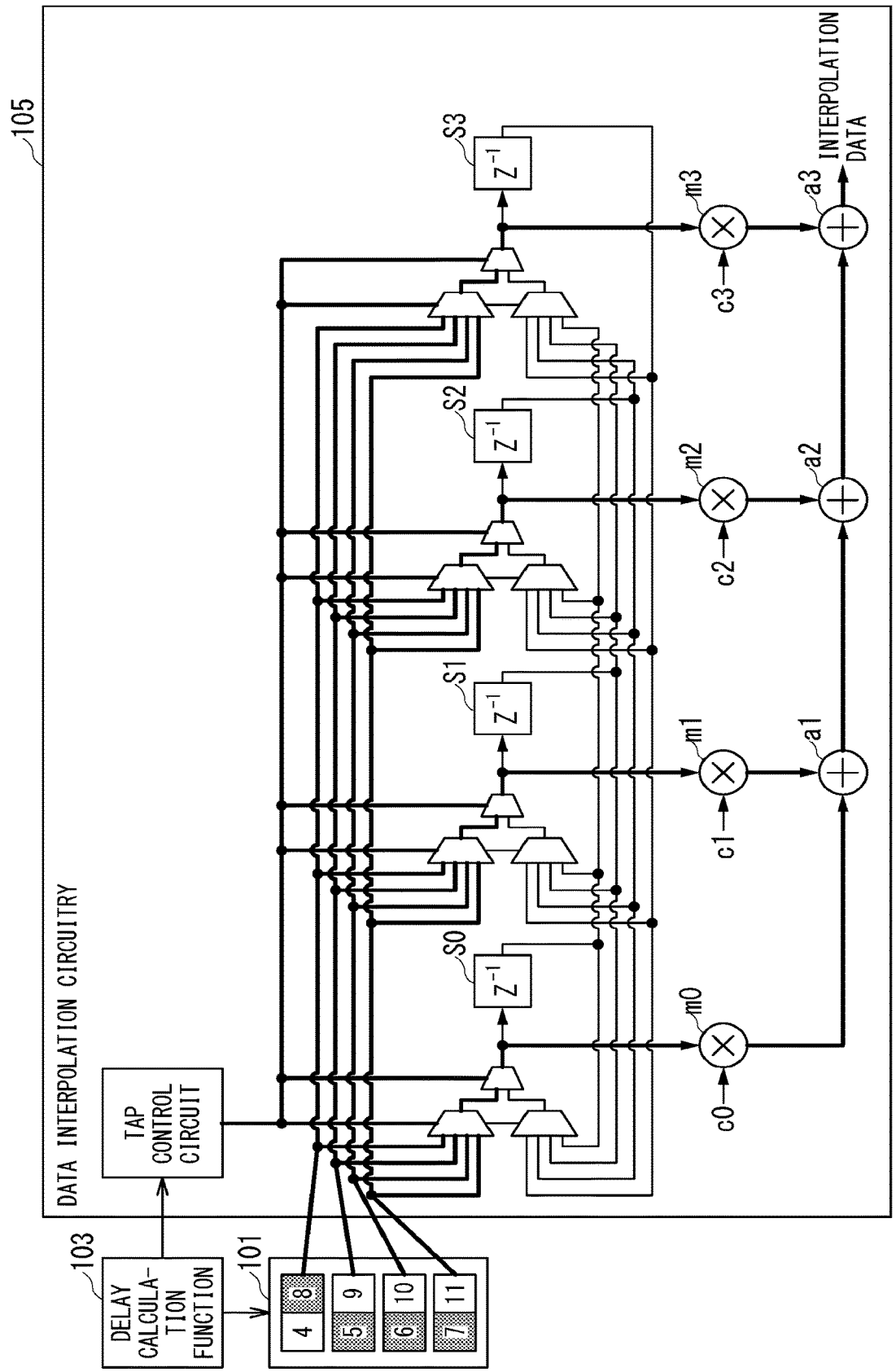
FIG. 8 is a diagram to illustrate a data interpolation method of the ultrasonic diagnostic apparatus relating to the first embodiment.

FIG. 8 is a diagram to illustrate a data interpolation method of the ultrasonic diagnostic apparatus 1 relating to the first embodiment. FIG. 8 shows an example of an interpolation filter included in the data interpolation circuitry 105. The interpolation filter comprises a tap control circuit, a multiplexer, a multiplication circuit, and an adding circuit.

The tap control circuit controls the multiplexer such that a plurality of pieces of reception data is inputted to the multiplication circuit in the order of time series.

The multiplexer selects reception data to be inputted to the multiplication circuit out of a plurality of pieces of reception data based on the control of the tap control circuit.

The multiplication circuit multiplies the reception data inputted from the multiplexer by a coefficient, and the adding circuit outputs interpolation data in which calculated results in the multiplication circuits are added respectively.

In the example of FIG. 8, S0 to S3 each indicate a unit delay circuit, m0 to m3 a multiplication circuit; c0 to c3 a coefficient of the multiplication circuit, and a trapezoid a multiplexer. The sampling data read from the memory circuitry 101 is inputted collectively into respective multiplexers. On the other hand, one sampling data which has been selected at a multiplexer by the control of the tap control circuit is inputted to the multiplication circuit. Coefficients (c0, c1, c2, c3) are set respectively in the multiplication circuits, and the pieces of inputted sampling data are weighted by the coefficients and are thereafter added by the adding circuit to calculate interpolation data.

FIG. 8 shows an example in which data is inputted to each multiplication circuit from the memory circuitry 101 via a path shown by a thick line. Note that although a unit delay circuit is shown in the example of FIG. 8, it can be omitted since sampling data can be inputted to the multiplication circuit by using a multiplexer.

The example of FIG. 8 shows a case in which interpolation data ("6.6") of the transducer A at a focal position A is calculated. The delay calculation function 103 determines sampling data needed for calculating the interpolation data ("6.6") to be "5", "6", "7", and "8", and determines the reading positions in the memory circuitry 101. When the sampling data needed for interpolation is determined by the delay calculation function 103, the reading positions of the sampling data from the memory circuitry 101 are determined at the same time. As shown by shadowing in the memory circuitry 101 of FIG. 8, the delay calculation function 103 determines addresses corresponding to the sampling points "5", "6", "7", and "8" and conveys them to the tap control circuit of the data interpolation circuitry 105.

As shown by thick lines in FIG. 8, the tap control circuit reads out the inputted sampling data from the memory and inputs them into the multiplication circuits m0 to m3. For example, when pieces of sampling data of "5", "6", "7", and "8" are inputted to the data interpolation circuitry 105, these four pieces of sampling data are inputted to m3 to m0. Although all the pieces of the sampling data of "5", "6", "7", and "8" are inputted to each multiplexer, sampling data is selected by the control of the tap control circuit and inputted to each multiplication circuit. As a result of such control, the multiplication circuit m3 is inputted with "5", m2 with "6", m1 with "7", and m0 with "8", respectively. The pieces of sampling data inputted to the multiplication circuits (m0, m1, m2, m3) are weighted by coefficients (c0, c1, c2, c3) set in the multiplication circuits, and thereafter added by the adding circuits (a1, a2, a3) to generate interpolation data. Note that the coefficients set in the multiplication circuits can be set in various ways depending on distances of the data to be interpolated from the sampling point. For example, when interpolating data to be calculated is to be positioned between "6" and "7" by using the sampling data of "5", "6", "7", and "8", if the position of data to be interpolated is closer to the sampling point "6" (for example, 6.2), concerning the coefficients (c1, c2) for the two pieces of central sampling data ("6" and "7"), the coefficient c1 which is multiplied with the data of "6" is set to be larger than the coefficient c2. On the other hand, if the position of the data to be interpolated is closer to the sampling point "7" (for example 6.8), the coefficient c2 which is to be multiplied with the data of "7" is set to be larger than the coefficient c1.

Note that in the above described example, since the data of the reference transducer is present in the sampling data, the interpolation processing can be omitted.

In this way, by adding all the calculated interpolation data for each focal position by the adder 200, a reception beam is formed for each focal position. For example, in the example of FIG. 5, interpolation data is calculated for each of "5" of the reference transducer and "6.6" of the transducer A for the focal point A. These pieces of interpolation data are added together to form a reception beam of the focal position A. Further, as to the focal position B which is the next focal position as well, interpolation data is calculated for each of "6" of the reference transducer and "8.3" of the transducer A, and these interpolation data are added together to form a reception beam.

In this way, for each of a plurality of focal positions included in a reception beam having a certain orienting direction, interpolation data is calculated (ST115), and a reception beam is formed (ST117). Based on the formed reception beam, an ultrasonic image is generated (ST119) and is displayed on a display 70 (ST121).

In this way, the ultrasonic diagnostic apparatus 1 relating to the first embodiment can acquire reception data concurrently and collectively from the memory by dividing the reception data and storing them in the memory circuitry 101. Moreover, in order to interpolate data which is apart from the immediately prior interpolation by one sampling point or more, the ultrasonic diagnostic apparatus 1 can read out necessary sampling data from the memory and calculate interpolation data. Therefore, it is possible to acquire data at a proper sampling interval, and prevent deterioration of image quality.

Second Embodiment

A second embodiment relates to a method of interpolation in which when reception data to be acquired from a memory overlaps, only difference data (a subtractive difference thereof) is acquired from the memory to perform interpolation.

Figure 9:
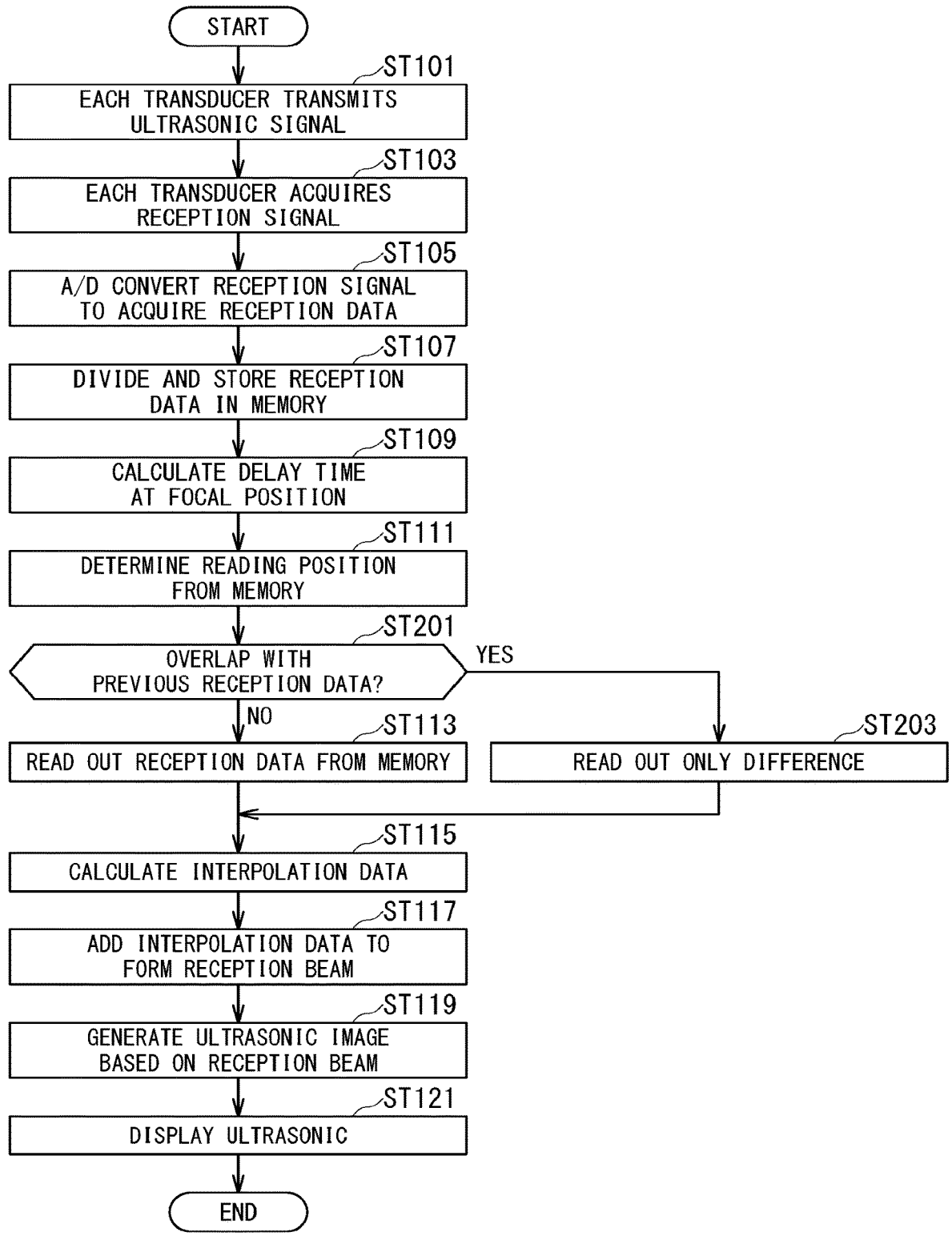
FIG. 9 is a flow chart showing an example of the operation of the ultrasonic diagnostic apparatus relating to the second embodiment.

FIG. 9 is a flow chart showing an example of the operation of the ultrasonic diagnostic apparatus 1 relating to the second embodiment. The steps in which the same operations as in the first embodiment are performed are denoted by the same numbers.

In ST201, the delay calculation function 103 judges whether or not the reception data to be used for the current interpolation overlaps with the reception data which has been used in the previous interpolation. When there is no overlap (No), interpolation data is generated by the method described regarding the first embodiment in ST115. On the other hand, when there is an overlap (Yes), the delay calculation function 103 determines the reading position of the reception data which constitutes a subtractive difference, and conveys it to the data interpolation circuitry 105.

In ST203, the data interpolation circuitry 105 reads out only the reception data of the subtractive difference from the memory circuitry 101.

Figure 10:
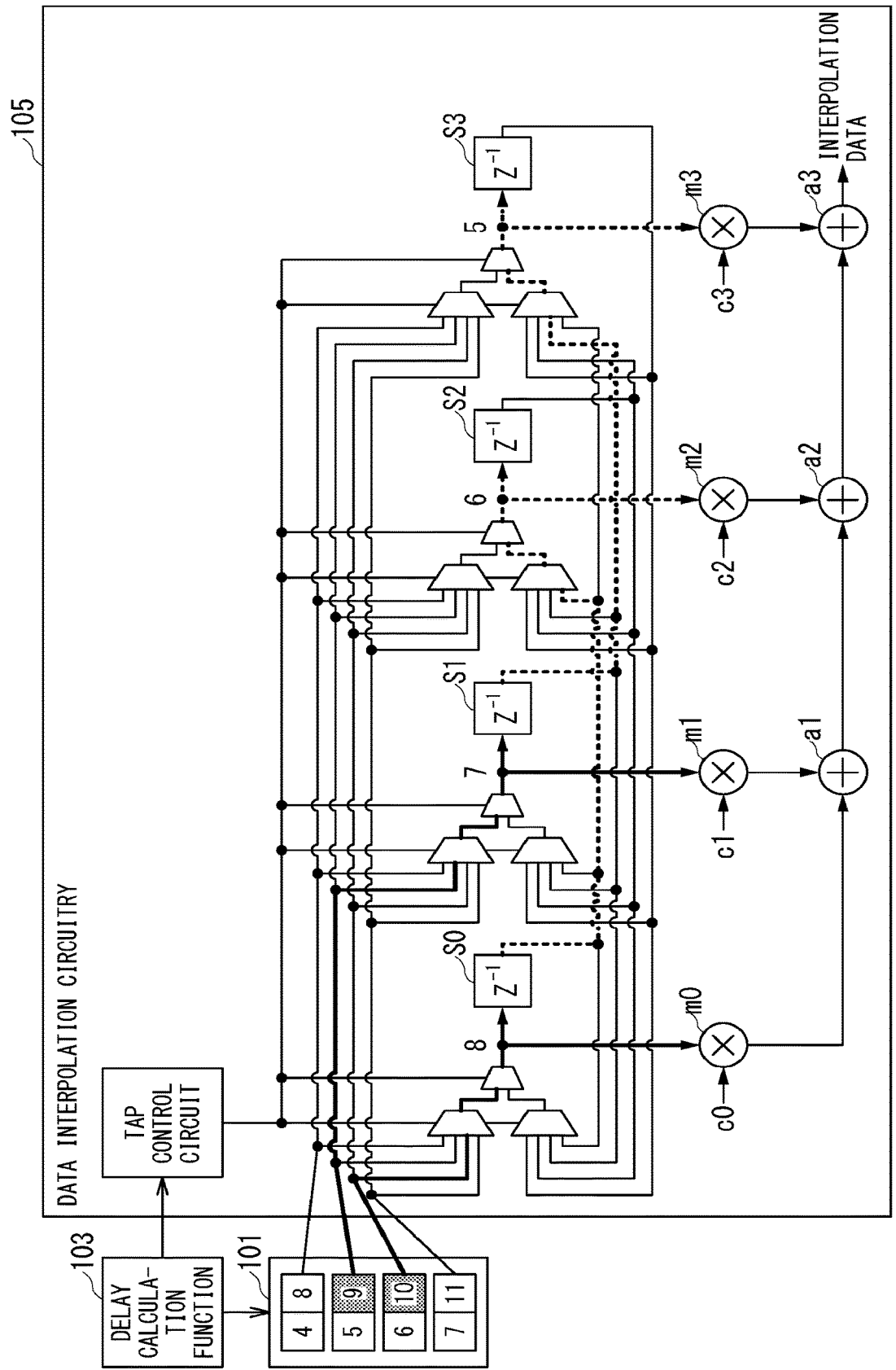
FIG. 10 is a diagram to illustrate a data interpolation method of the ultrasonic diagnostic apparatus relating to the second embodiment.

FIG. 10 is a diagram to illustrate a data interpolation method of the ultrasonic diagnostic apparatus 1 relating to the second embodiment. As with the example of FIG. 8, the data interpolation circuitry 105 shown in FIG. 10 comprises a tap control circuit, multiplexers, multiplication circuits, and adding circuits.

In the example of FIG. 10, the number of the sampling point used in the previous interpolation is shown in the upper left portion of each of unit delay circuits S0 to S3, and a state after the interpolation data of "6.6" position is calculated is shown. That is, the reception data "5" which is used for "6.6" interpolation exemplified in FIG. 7A is stored in the unit delay circuit S3; "6" in a unit delay circuit S2; "7" in a unit delay circuit S1; and "8" in a unit delay circuit S0, respectively.

When data to be calculated next is interpolation data at a position of "8.3", it is necessary that pieces of sampling data of "7", "8", "9", and "10" are read into the data interpolation circuitry 105. Here, the delay calculation function 103 judges that since pieces of sampling data of "7" and "8" are overlapped between the previous and current interpolations, pieces of data which need to be newly read from memory circuitry 101 are sampling data of "9" and "10".

Then, as shown by dotted lines in FIG. 10, the tap control circuit of the data interpolation circuitry 105 controls the multiplexers located on the left sides of the unit delay circuits S2 and S3 so as to move "7" from the unit delay circuit S1 to the unit delay circuit S3, and move "8" from the unit delay circuit S0 to the unit delay circuit S2 of the overlapping data of "7" and "8". As a result of such control, pieces of overlapping sampling data of "7" and "8" are stored in the unit delay circuits S2 and S3, respectively.

On the other hand, pieces of sampling data of "9" and "10" are newly read from the memory circuitry 101 and stored in the unit delay circuits S0 and S1. As shown by thick lines in FIG. 10, "9" is stored in the unit delay circuit S1, and "10" is stored in the unit delay circuit S0. In this way, based on the control of the tap control circuit, "9" and "10" are selectively inputted to the unit delay circuits S1 and S0 by the multiplexers located at the left sides of the unit delay circuits S1 and S0.

The pieces of sampling data stored in the unit delay circuits S0 to S3 are inputted to the multiplication circuits m0 to m3. Coefficients (c0, c1, c2, c3) are respectively set in the multiplication circuits, and the pieces of sampling data are weighted by these coefficients, and thereafter added by the adding circuits (a1, a2, a3) to calculate interpolation data ("8.3").

In this way, since the number of pieces of data that are read out from the memory circuitry 101 by the data interpolation circuitry 105 decreases as a result of reusing the sampling data, which has been used in the previous interpolation, in the next interpolation processing, it is possible to increase the speed of the processing in the data interpolation circuitry 105. Moreover, since the number of access to the memory circuitry 101 decreases, it is possible to suppress power consumption.

Note that although the first and second embodiments have been described by taking an example of the ultrasonic diagnostic apparatus 1, interpolating processing units and interpolation processing methods, which have the equivalent configuration with that of the delay controller 100 of the ultrasonic diagnostic apparatus 1, may be applied to the signal processing such as image processing and voice processing.

For example, one example of such image processing includes image compression processing. As an algorithm for compression processing, there is one that determines data, which is spaced apart by one or more sampling points from the immediately prior interpolation, by interpolation. To be specific, there is method of inputting respective pixels as reception data, and determining necessary sampling points depending on the positional relationship on the image of the pixels, to create interpolation data. In such a case, a method similar to the delay controller 100 which has been described in the ultrasonic diagnostic apparatus 1 relating to the present embodiment can be applied. In this way, the interpolation processing unit and interpolation processing method relating to the present embodiment are applicable to signal processing for interpolating various data such as numerical values, images, videos, or voices which are collected continuously in the time series.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Note that the term "processor" of the present embodiments means, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, an FPGA (Field Programmable Gate Array), and the like. A processor achieves various types of functions by reading out programs stored in memory circuitry and by implementing the programs.

In addition, programs may be directly installed in the circuit of a processor instead of storing programs in the memory circuitry. In this case, the processor achieves various types of functions by reading out programs stored in its own circuit and implementing the programs.

Although a case where a single processing circuitry achieves each function has been explained above, this is only an example. As another example, the processing circuitry may be configured by combining a plurality of mutually independent processers so that each function is achieved by each processer that executes the corresponding program.

When a plurality of processors are used, a memory medium for storing programs may be disposed for each processer, or a single memory circuitry may collectively store the programs corresponding to the functions of all the processors.

The invention claimed is:

1. An ultrasonic diagnostic apparatus, comprising:
   a plurality of transducers configured to transmit an ultrasonic wave and receive a reflected wave from an interior of an object;
   a memory circuitry configured to store a plurality of pieces of reception data in an order of reception, the plurality of pieces of reception data being sampled at a predetermined sampling interval and being continuous in a time series, and configured to permit reading positions to be specified in an order different from the order of reception;

a processing circuitry configured to calculate a delay time to be set for every reception data from each of the plurality of transducers, and configured to calculate, based on the delay time, reading positions for acquiring from the memory circuitry a plurality of pieces of reception data to be used for calculating interpolation data;

a data interpolation circuitry configured to calculate interpolation data based on the plurality of pieces of reception data acquired from the calculated reading positions of the memory circuitry; and an image generating circuitry configured to generate an ultrasonic image based on a reception beam formed by using the interpolation data, wherein the processing circuitry is configured to calculate the reading positions for acquiring the current reception data corresponding to a sampling point being shifted by two or more of the predetermined sampling interval from an immediately previous sampling point while skipping calculating reading positions for acquiring reception data being shifted by one of the predetermined sampling interval.

2. The ultrasonic diagnostic apparatus according to claim 1, wherein
the image generating circuitry generates the ultrasonic image based on a reception beam formed by using both the reception data themselves and the interpolation data.

3. The ultrasonic diagnostic apparatus according to claim 1, further comprising:
a display displays the ultrasonic image which is generated by the image generating circuitry.

4. The ultrasonic diagnostic apparatus according to claim 1, wherein
the memory circuitry stores the plurality of pieces of reception data being received continuously in the time series such that the plurality of pieces of reception data are divided into a number of data sets, the number corresponding to a number of the pieces of reception data to be used for calculating the interpolation data.

5. The ultrasonic diagnostic apparatus according to claim 1, wherein
when reception data used in a previous interpolation processing and the current reception data overlap, the data interpolation circuitry acquires only difference data between the reception data used in the previous interpolation processing and the current reception data from the memory circuitry, and calculates interpolation data by using both the difference data and overlapping reception data.

6. The ultrasonic diagnostic apparatus according to claim 1, wherein
the data interpolation circuit calculates the interpolation data based on a coefficient according to positions of two reception data between which the interpolation data to be calculated is to be positioned.

7. The ultrasonic diagnostic apparatus according to claim 1, wherein
the data interpolation circuitry includes:
a tap control circuit;
a multiplexer;
a multiplication circuit; and
an adding circuit, wherein the tap control circuit connects with the multiplexer and controls the multiplexer such that the plurality of pieces of reception data, which are acquired from the memory circuitry, are inputted to the multiplication circuit in the order of the reception;
the multiplexer connects with the multiplication circuit and selects, based on control of the tap control circuit, reception data to be inputted to the multiplication circuit out of the plurality of pieces of reception data acquired from the memory circuitry,
the multiplication circuit connects with the adding circuit and multiplies each of the reception data inputted from the multiplexer by a corresponding coefficient; and
the adding circuit adds results calculated in the multiplication circuit and outputs the interpolation data.

8. An interpolation processing unit for interpolating a part of data collected continuously in a time series, the interpolation processing unit comprising:
a memory circuitry configured to store data collected continuously in the time series at a predetermined sampling interval in an order of collection, and configured to permit reading positions to be specified in an order different from the order of the collection;
a processing circuitry configured to calculate reading positions for acquiring from the memory circuitry a plurality of pieces of data, out of the data collected continuously in the time series, to be used for calculating interpolation data; and
a data interpolation circuitry configured to calculate interpolation data based on the plurality of pieces of data acquired from the calculated reading positions of the memory circuitry, wherein
the processing circuitry is configured to calculate the reading positions for acquiring the current reception data corresponding to a sampling point being shifted by two or more of the predetermined sampling interval from an immediately previous sampling point while skipping calculating reading positions for acquiring reception data being shifted by one of the predetermined sampling interval.

9. The interpolation processing unit according to claim 8, wherein
the data interpolation circuitry includes:
a tap control circuit;
a multiplexer;
a multiplication circuit; and
an adding circuit, wherein
the tap control circuit connects with the multiplexer and controls the multiplexer such that the plurality of pieces of data, which are acquired from the memory circuitry, are inputted to the multiplication circuit in the order of the collection;
the multiplexer connects with the multiplication circuit and selects, based on control of the tap control circuit, the data to be inputted to the multiplication circuit out of the plurality of pieces of data acquired from the memory circuitry,
the multiplication circuit connects with the adding circuit and multiplies each of the data inputted from the multiplexer by a corresponding coefficient; and
the adding circuit adds results calculated in the multiplication circuit and outputs the interpolation data.

10. An interpolation processing method of interpolating a part of data collected continuously in a time series, the interpolation processing method comprising:
causing a memory circuitry to store data collected continuously in the time series at a predetermined sampling interval in an order of collection, the memory circuitry being able to permit reading positions to be specified in an order different from the order of the collection;

calculating reading positions for acquiring from the memory circuitry a plurality of pieces of data, out of the data collected continuously in the time series, to be used for calculating interpolation data; and calculating interpolation data based on the plurality of pieces of data acquired from the calculated reading positions of the memory circuitry, wherein the step of calculating reading positions includes a step of calculating the reading positions for acquiring the current reception data corresponding to a sampling point being shifted by two or more of the predetermined sampling interval from an immediately previous sampling point while skipping calculating reading positions for acquiring reception data being shifted by one of the predetermined sampling interval.

11. The interpolation processing method according to claim 10, comprising:

when reception data used in a previous interpolation processing and reception data needed in a current interpolation processing overlap, the method comprise acquiring only difference data between the reception data used in the previous interpolation processing and the reception data needed in the current interpolation processing, and calculating interpolation data by using both the difference data and overlapping reception data.

12. An ultrasonic diagnostic apparatus, comprising:

a plurality of transducers configured to transmit an ultrasonic wave and receive a reflected wave from an interior of an object;

memory circuitry configured to store a plurality of pieces of reception data in an order of reception, the plurality of pieces of reception data being sampled at a predetermined sampling interval and being continuous in a time series, and configured to permit reading positions to be specified in an order different from the order of reception;

processing circuitry configured to calculate a delay time to be set for every reception data from each of the plurality of transducers, to calculate, based on the delay time, reading positions for acquiring from the memory circuitry a plurality of pieces of reception data to be used for calculating interpolation data, and specify calculated reading positions to be read from the memory circuitry;

data interpolation circuitry configured to calculate interpolation data based on the plurality of pieces of reception data acquired from the calculated reading positions of the memory circuitry; and image generating circuitry configured to generate an ultrasonic image based on a reception beam formed by using the interpolation data, wherein the processing circuitry is configured to:

calculate first reading positions for acquiring current reception data corresponding to a sampling point being shifted by two or more of the predetermined sampling interval from an immediately previous sampling point, determine whether the calculated first reading positions overlap with previously calculated reading positions for acquiring reception data corresponding to the immediately preceding sampling point, and specify only those of the calculated first reading positions other than overlapping reading positions to be read from the memory circuitry.

13. The ultrasonic diagnostic apparatus according to claim 12, wherein the data interpolation circuitry includes:
a tap control circuit;
a multiplexer;
a multiplication circuit; and
an adding circuit, wherein the tap control circuit connects with the multiplexer and controls the multiplexer such that pieces of reception data to be acquired from the memory circuitry, are inputted to the multiplication circuit in the order of the reception, the multiplexer connects with the multiplication circuit and selects, based on control of the tap control circuit, reception data to be inputted to the multiplication circuit out of the plurality of pieces of reception data acquired from the memory circuitry, the multiplication circuit connects with the adding circuit and multiplies each of the reception data inputted from the multiplexer by a corresponding coefficient; and the adding circuit adds results calculated in the multiplication circuit and outputs the interpolation data.

14. The ultrasonic diagnostic apparatus according to claim 13, wherein when overlapping reading positions are determined, the tap control circuit controls the multiplexer such that pieces of reception data corresponding to the overlapping reading positions are inputted to the multiplication circuit without being newly read from the memory circuitry and reception data corresponding to those of the calculated first reading positions other than overlapping reading positions are inputted to the multiplication circuit after being read from the memory circuitry.

* * * * *